United States Patent [19]

Starks

[11] 4,060,561
[45] Nov. 29, 1977

[54] METHOD FOR THE PREPARATION OF TRIMETHYLHYDROQUINONE

[75] Inventor: Charles M. Starks, Ponca City, Okla.

[73] Assignee: Continental Oil Company, Ponca City, Okla.

[21] Appl. No.: 724,788

[22] Filed: Sept. 20, 1976

[51] Int. Cl.$^2$ ............................................. C07C 39/08
[52] U.S. Cl. ............................. 260/621 F; 260/621 R
[58] Field of Search ............... 260/621 R, 625, 613 D, 260/621 F

[56]  References Cited
U.S. PATENT DOCUMENTS

| 2,091,483 | 8/1937 | Olin | 260/621 F |
| 2,289,886 | 7/1942 | Schmerlin | 260/621 F |
| 2,697,732 | 12/1954 | Mavity | 260/613 D |
| 3,256,336 | 6/1966 | Lange | 260/592 |

Primary Examiner—James O. Thomas, Jr.
Assistant Examiner—W. B. Lone
Attorney, Agent, or Firm—Cortlan R. Schupbach, Jr.

[57] ABSTRACT

Trimethylhydroquinone is prepared by reacting 4-methoxyphenol with methanol over MgO or MgO promoted with oxides of aluminum, uranium, titanium, cerium, manganese, zinc, and iron at temperatures of from about 350° C to about 550° C and pressures up to about 1,000 pounds per square inch gauge.

11 Claims, No Drawings

METHOD FOR THE PREPARATION OF TRIMETHYLHYDROQUINONE

This invention relates to a method for the preparation of trimethylhydroquinone. More specifically, this invention relates to a method for preparing trimethylhydroquinone by reacting 4-methoxyphenol with methanol over magnesium oxide catalysts or aluminum oxide catalysts promoted with oxides of various metals at pressures of up to 1,000 psig and temperatures of from 350° C to 550° C.

Trimethylhydroquinone is well-known as a valuable intermediate in the synthesis of Vitamin E. Many methods have been given for its production in the chemical literature. However, industrial quantities of the trimethylhydroquinone are prepared using a sequence of reactions beginning with phenol. The phenol is methylated, usually using methanol in the presence of a catalyst to form 2,3,6 trimethylphenol, which is then oxidized to form trimethylquinone, which in turn is reduced to form trimethylhydroquinone. The process is set forth schematically below:

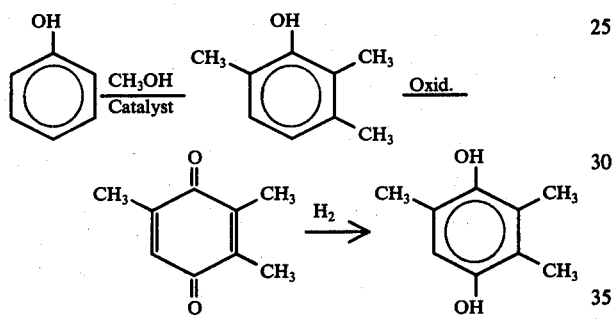

It will be readily apparent that the process is involved, lengthy, and expensive. It would therefore be of great benefit to provide a process for the production of this valuable material which is less expensive and more easily carried out.

It has long been known that hydroxyaromatics can be reacted with alcohols in the presence of a catalyst. Such processes are shown in U.S. Pat. Nos. 2,615,051, and 2,782,239 both of which show the reaction of hydroquinone and methanol to make methoxyphenol. These references, however, are silent as to the production of trimethylhydroquinone. Hydroquinone and methanol cannot be directly methylated to form trimethylohydroquinone.

It is therefore an object of the present invention to provide a method for the production of trimethylhydroquinone. Other objects will become apparent to those skilled in this art as the description proceeds.

It has now been discovered that trimethylhydroquinone can be prepared by reacting 4-methoxyphenol (p-hydroxyanisole) with methanol over magnesium oxide or alumina catalysts optionally promoted with oxides of uranium, titanium, cerium, manganese, zinc, and iron at temperatures of from about 350° C to about 550° C and pressures of up to about 1,000 pounds per square inch gauge (psig).

It is surprising in view of the fact that hydroquinone alone cannot be reacted with methanol to produce trimethylhydroquinone that the present invention will produce trimethylhydroquinone. In addition, it is surprising that when using 4-methoxyphenol as a starting material some hydroquinone can be added to produce trimethylhydroquinone. While the amount of trimethylhydroquinone which can be added without adverse effect will vary depending upon the reaction conditions encountered normally up to about 25% of hydroquinone can be included in the reaction without adverse effects.

Generally, the reaction of the instant invention is set forth in schematic form below:

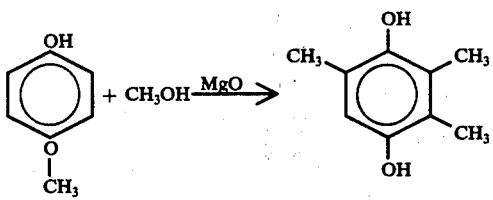

The reaction also forms several by-products including those set forth in schematic form below:

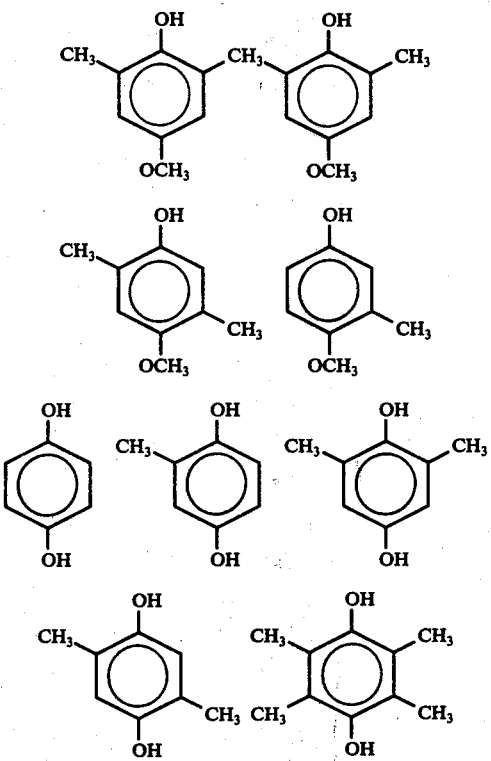

The catalysts used are essentially totally magnesium oxide or aluminum oxide or a mixture of these, but catalysts also containing other ingredients can be used. For example, silica, alumina, titania, cerium oxide manganese oxide, iron oxide, zinc oxide, vanadium oxide uranium oxide, and other metal oxides in the rare earth series can be used to promote the reaction, whether in pure form or in mixtures.

The reaction is most advantageously carried out at temperatures in the range of from about 250° C to about 550° C. However, preferred temperatures are normally in the range of about 350° C to 525° C. While pressures can vary up to about a thousand pounds per square inch gauge, preferred pressures are normally from about 200 to about 500 psig.

The reaction can be carried out either batch-wise or continuously. When carried out in a continuous flow reactor, normally a liquid hourly space velocity (LHSV) of from about 0.1 to about 50 will be used. An LHSV of from about 0.2 to about 10 is preferred. The reaction normally requires a mole ratio of 4-methoxyphenol to methanol of from about 1 to about 0.25 up to about 1 to 20 respectively.

Water added to the feed stream is not desirable when alumina catalysts are used, but water presence tends to increase magnesium oxide catalyst useful life in the present reactions. Normally such water is present in amounts up to about 15 percent by weight. Water is not critical for the present reaction.

The invention is more concretely described with reference to the examples below wherein all parts and percentages are by weight unless otherwise specified. It is emphasized that the examples are intended to illustrate the present invention and not to limit it. Example 1 shows a typical reaction reacting methanol with 4-methoxyphenol over magnesium oxide. Examples 2 through 3 show a typical reaction carried out using aluminum oxide catalysts and continuous flow reactor conditions. Example 5 is a comparative example showing the ineffectiveness of using a hydroquinone feed in the process of the instant invention.

EXAMPLE 1

A mixture of 21.05 grams of 4-methoxyphenol, 27.2 grams of methanol, and 1.7 grams of water was pumped continuously at an LHSV of 0.25 over a period of one hour through a bed of magnesium oxide catalyst (Harshaw MgO601 sold by Harshaw Chemical Company) pellets contained in a 4-inch section of a stainless steel pipe 2 inches in diameter. The reactor was heated in a salt bath to 503° C. The product from the reaction was cooled and collected. After standing overnight, the reaction mixture had separated into a aqueous phase, a liquid organic phase, and a solid organic phase. Analysis of the organic phases by gas chromatography is shown in Table 1.

Table 1

| Product | % in Product | |
|---|---|---|
| | liquid product | solid product |
| 4-methoxyphenol | 23.2 | 14.3 |
| 2-methyl-4-methoxyphenol | 10.3 | 6.1 |
| 3-methyl-4-methoxyphenol | 9.4 | 5.6 |
| 2,6-dimethyl-4-methoxyphenol | 33.0 | 23.7 |
| 2,6-dimethylhydroquinone | 3.5 | 12.3 |
| 2,5-dimethylhydroquinone | 3.8 | 12.3 |
| hydroquinone | 6.4 | 7.4 |
| trimethylhydroquinone | 9.3 | 12.8 |
| tetramethylhydroquinone | 1.1 | 17.6 |

A majority of the by-products produced can be recycled without detrimental effect to the reactor for further conversion to form trimethydroquinone.

EXAMPLE 2

A feed mixture of 434 grams of 4-methoxyphenol and 224 grams of methanol was pumped at a rate of 104 ml per minute under 300 psig backpressure into a stainless steel tubular reactor having dimensions of 24 inches by ½ inch. The reactor contained 66.2 grams of aluminum oxide catalysts (CATAPAL, sold by Continental Oil Company) in the form of 1/16 inch extrudate pellets. The reactor was heated to increasingly higher temperatures to ascertain the effect of temperature on product distribution. Results of this experiment were determined using gas-liquid chromotography (GLC). Table 2 shows the product distribution from the methalation of 4-methoxyphenol at various temperatures over aluminum oxide catalysts.

Table 2

| Component | Feed | Product Composition Area % at Reactor Temp. of | | | | |
|---|---|---|---|---|---|---|
| | | 250° C | 300° C | 325° C | 380° C | 390° C |
| Methanol, water and dimethyl ether | 38.38 | 38.11 | 38.10 | 39.30 | 36.76 | 36.86 |
| CH$_3$O—⌬—OCH$_3$ | — | 6.90 | 8.15 | 13.38 | 7.70 | 8.87 |
| HO—⌬—OCH$_3$ | 61.51 | 53.68 | 38.11 | 17.00 | 10.02 | 11.06 |
| Methyl ethers of HO—⌬(CH$_3$)—OH | — | 0.43 | 2.61 | 1.94 | 3.94 | 4.65 |
| HO—⌬—OH | 0.12 | 0.88 | 12.02 | 11.90 | 9.86 | 8.94 |
| HO—⌬(CH$_3$)—OH | — | — | 1.01 | 5.71 | 7.12 | 6.86 |
| Isomeric dimethyl hydroquinones and their ethers | — | — | — | 5.89 | 11.27 | 11.81 |
| Trimethylhydroquinone ethers | — | — | — | 1.38 | 3.45 | 2.19 |
| Trimethylhydroquinone | — | — | — | 1.82 | 4.77 | 4.25 |
| Tetromethylhydroquinone | — | — | — | 0.84 | 1.83 | 1.66 |
| Higher Compounds | — | — | — | 0.84 | 3.28 | 2.85 |

EXAMPLE 3

All of the products obtained in Example 2 above, less retained samples for analysis, were mixed into a single distillation flask, the total charge comprising 566.2 grams. The contents of the flask were fractionally distilled through a 4-foot spinning band column with the results shown in Table 3. The data obtained is from the fractional distillation of combined methylate as determined by gas chromatography analysis.

ing these cuts with 127.3 grams of fresh methanol to form a feed mixture. The feed mixture was pumped into a reactor as described in Example 2 above at a rate of 100 ml per hour. The reactor contained 67.6 grams of fresh aluminum oxide catalyst as described above. The reaction was conducted at a temperature of 375° C during the first half hour at the end of which time sample 1 was obtained. The temperature of the reaction was then raised to 412° C for a 5 hour run during which time samples 2 through 6 were taken, on a hourly basis. The Table 3

| | -CUT- | | | | | | | | | |
|---|---|---|---|---|---|---|---|---|---|---|
| | 1 | 2 | 3 | 4 | 5 | 6 | 7 | 8 | 9 | 10 |
| Boiling Temp ° C | 59–100 | 100–110 | 110–138 | 138–154 | 154–157 | 157–158 | 158–159 | 159–161 | 161–187 | 187–198 |
| at pressure mm Hg | 760 | 30 | 30 | 30 | 30 | 30 | 30 | 30 | 30 | 30 |
| Weight of Cut, g., [1] | 146.5 | 32.15 | 32.8 | 32.0 | 31.7 | 34.1 | 34.7 | 33.4 | 34.1 | 61.0 |
| Composition of Cut Area % | | | | | | | | | | |
| methanol, CH$_3$OCH$_3$,H$_2$O | 100 | 12.04 | 3.54 | 2.49 | 0.87 | 1.36 | 0 | 0 | 0 | 0 |
| CH$_3$O—⟨O⟩—OCH$_3$ | — | 65.84 | 51.90 | 42.06 | 9.30 | 3.32 | 0.68 | — | — | 0.21 |
| CH$_3$—⟨O⟩—OH | — | 12.03 | 17.39 | 20.59 | 70.76 | — | — | — | — | 7.54 |
| HO—⟨O⟩—OH | — | — | 10.69 | 16.60 | 70.76 | — | — | — | — | 7.54 |
| CH$_3$—⟨O⟩(CH$_3$)—OH | — | 6.17 | 6.81 | 5.99 | 1.21 | — | — | — | — | 4.56 |
| CH$_3$O—⟨O⟩(CH$_3$)—OH | — | 1.41 | 1.60 | 1.79 | 0.97 | — | — | — | — | 5.65 |
| HO—⟨O⟩(CH$_3$)—OH | — | 0.44 | 3.06 | 4.23 | 9.32 | 75.07 | 75.80 | 72.23 | 47.01 | 10.64 |
| Dimethylhydroquinone isomers and ethers | — | 1.99 | 1.64 | 1.93 | 1.80 | 12.73 | 14.16 | 15.74 | 21.52 | 23.91 |
| Trimethylhydroquinone ethers | — | 0.08 | 3.24 | 4.07 | 5.11 | — | — | — | 9.43 | 10.24 |
| Trimethylhydroquinone | — | — | 0.13 | 0.14 | 0.44 | 6.67 | 6.41 | 6.90 | 11.32 | 24.49 |
| Tetromethylhydroquinone | — | — | — | 0.11 | 0.22 | 0.85 | 1.09 | 1.74 | 8.95 | 5.25 |
| Higher Boiling capacity | — | — | — | — | — | — | 1.86 | 3.39 | 1.77 | 7.51 |

[1]Products collected in coldtrap weighed 17.6 g. Residue from distillation weighed 52.8 g.

EXAMPLE 4

The recycle of lower methylated and unmethylated products was examined by obtaining cuts 2–9 from the distillation described in Example 3, combining and mixing these cuts with 127.3 grams of fresh methanol to product distribution from these runs were determined by gas-liquid chromatography and are listed in Table 4. The table shows the product distribution from the methylation of the hydroquinone derivatives mixture.

Table 4

| | Sample No. | | | | | |
|---|---|---|---|---|---|---|
| | 1 | 2 | 3 | 4 | 5 | 6 |
| Methanol, CH$_3$OCH$_3$,H$_2$O | 15.16 | 39.00 | 37.39 | 36.48 | 35.61 | 38.40 |
| Unknowns | 6.95 | 2.56 | 2.30 | 2.32 | 1.72 | 1.94 |
| CH$_3$O—⟨O⟩—OCH$_3$ | 5.55 | 8.77 | 8.81 | 9.33 | 10.18 | 10.38 |

Table 4-continued

| | Sample No. | | | | | |
|---|---|---|---|---|---|---|
| | 1 | 2 | 3 | 4 | 5 | 6 |
| CH₃O—⟨O⟩—OCH₃ with CH₃ | 5.47 | 6.79 | 7.04 | 7.18 | 7.54 | 7.90 |
| CH₃O—⟨O⟩—OH | 8.02 | 4.42 | 4.25 | 3.91 | 3.72 | 4.38 |
| CH₃O—⟨O⟩—OH with CH₃ | — | 1.46 | 1.82 | — | 1.75 | 1.90 |
| HO—⟨O⟩—OH | 9.89 | 6.17 | 7.00 | 7.26 | 7.93 | 7.40 |
| CH₃O—⟨O⟩—OH with CH₃,CH₃ | 3.25 | 2.34 | — | 2.99 | 53 | 2.88 |
| HO—⟨O⟩—OH with CH₃,CH₃ | 18.36 | 7.26 | 9.04 | 8.92 | 8.18 | 8.91 |
| Dimethylhydroquinone isones, ethers | 9.23 | 8.16 | 9.13 | 9.58 | 8.49 | 8.00 |
| Trimethylhydroquinone | 6.56 | 4.14 | 4.29 | 4.82 | 4.40 | 4.73 |
| Tetramethylhydroquinone | 0.42 | 4.00 | 3.47 | 3.72 | 3.43 | 2.81 |
| Higher Materials | 11.14 | 4.93 | 5.46 | 3.45 | 3.52 | 0.37 |

The trimethyhydroquinone can be easily separated from other methylated quinones such as in cut 10 by using methods well-known to those skilled in this art, such as crystallization from solution.

EXAMPLE 5

A feed mixture made up from 50g hydroquinone, 145g methanol, and 5.7g of water was pumped into a catalyst bed containing 128 ml of magnesium oxide catalyst (as described in Example 1) at a rate of 46 ml per hour. The catalyst bed temperature was maintained at 495°-503° C. After pumping in the feed for 3 hours no liquid or solid product had been produced, although a large amount of gas was produced, mostly methane, carbon monoxide and hydrogen. After this time the catalyst bed was cooled to room temperature and examined. The catalyst was completely covered with coke. All the hydroquinone and/or its reaction products remained on the catalyst and appeared to be carbonized. The carbon appeared to catalyze the decomposition of methanol to yield the gaseous products.

The present invention thus provides a method for the production of trimethyhydroquinone which requires fewer steps, less expense, and less process time than prior art procedures. By-products formed can be recycled without separation, each pass through the reactor producing more rimethylhydroquinone. It has been surprisingly found that while hydroquinone cannot be directly methylated to trimethylhydroquinone, some hydroquinone can be directly methylated in minor amounts when in the presence of 4-methoxyphenol.

While certain embodiments and details have been shown for the purpose of illustrating this invention, it will be apparent to those skilled in this art that various changes and modifications may be made herein without departure from the spirit or the scope of the invention.

I claim:

1. A method for the production of trimethylhydroquinone comprising reacting 4-methoxyphenol with methanol over catalysts selected from the group consisting of magnesium oxide and aluminum oxide at temperatures of from about 350° C to about 550° C at pressures of from about atmospheric to about 1,000 psig.

2. A method as described in claim 1 above wherein in addition the catalysts are promoted with oxides of uranium, titanium, cerium, manganese, zinc and iron.

3. A method as described in claim 2 above wherein the 4-methoxyphenol contains up to about 25 weight percent hydroquinone.

4. A method as described in claim 2 wherein the mole ratio of 4-methoxyphenol to methanol ranges from about 0.05 to about 4.

5. A method as described in claim 4 wherein the reaction is carried out in a continuous flow reactor.

6. A method as described in claim 5 wherein the LHSV is from about 0.1 to about 50.

7. A method as described in claim 2 wherein the by-products of the reaction are separated and recycled for inclusion with 4-methoxyphenol feed.

8. A method as described in claim 2 wherein up to about 15 weight percent water is present in the feed, based upon the total feed weight.

9. A method as described in claim 2 wherein the trimethylhydroquinone produced is 2,3,6-trimethylhydroquinone, the catalyst is magnesium oxide, the reaction pressure is from about 200 to about 500 pounds per square inch gauge.

10. A method as described in claim 9 wherein the reaction is carried out continuously at a liquid hourly space velocity from about .2 to about 10.

11. A method as described in claim 10 wherein in addition the feed stream contains up to about 15 weight percent water based upon the total feed weight.

* * * * *